United States Patent [19]

Brown et al.

[11] 4,210,418
[45] Jul. 1, 1980

[54] CONTAINER FOR IMMUNOCHEMICAL AND ENZYMATICAL DETERMINATIONS OR PROCEDURES

[75] Inventors: James L. Brown, House Springs; Wayne H. T. Lin, Chesterfield; James W. Woods, Creve Coeur, all of Mo.

[73] Assignee: Mallinckrodt, Inc., St. Louis, Mo.

[21] Appl. No.: 758,364

[22] Filed: Jan. 10, 1977

Related U.S. Application Data

[63] Continuation-in-part of Ser. No. 718,694, Aug. 30, 1976, abandoned.

[51] Int. Cl.² ............................................. G01N 33/16
[52] U.S. Cl. ................................. 23/230 B; 23/230.3; 23/915; 23/920; 435/7; 435/296; 422/57; 422/58; 424/1; 424/12; 427/2

[58] Field of Search ..................... 23/230 B, 259, 292, 23/230.6, 230.3; 195/103.5 A, 127; 424/1, 1.5, 12; 427/2

[56] References Cited

U.S. PATENT DOCUMENTS

| | | | |
|---|---|---|---|
| 3,615,222 | 10/1971 | Mead | 23/259 |
| 3,646,346 | 2/1972 | Catt | 424/12 X |
| 3,770,380 | 11/1973 | Smith | 23/230 B |
| 3,826,619 | 7/1974 | Bratu, Jr. et al. | 23/259 |
| 3,867,517 | 2/1975 | Ling | 23/230.3 |

*Primary Examiner*—R. E. Serwin
*Attorney, Agent, or Firm*—Roy J. Klostermann

[57] ABSTRACT

A container useful in immunochemical and enzymatical determinations or procedures.

36 Claims, 3 Drawing Figures

U.S. Patent  Jul. 1, 1980  4,210,418
FIG. 2
FIG. 1
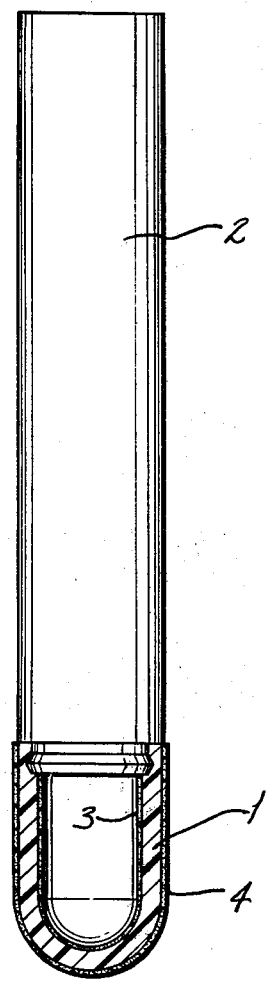
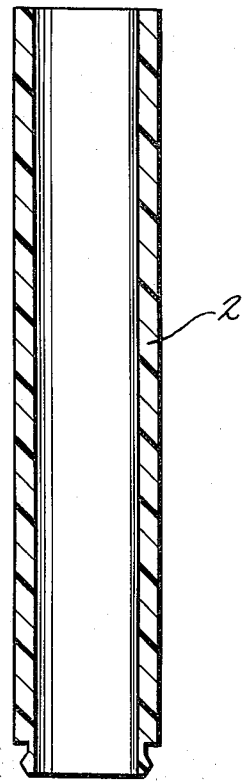
FIG. 3
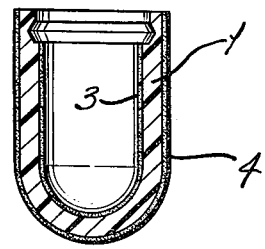

CONTAINER FOR IMMUNOCHEMICAL AND ENZYMATICAL DETERMINATIONS OR PROCEDURES

Related Cases

This application is a continuation-in-part of U.S. application Ser. No. 718,694 filed Aug. 30, 1976 now abandoned.

BACKGROUND OF THE INVENTION

1. Field of the Invention

This invention relates to containers such as test tubes suitable for use in solid phase immunochemical and enzymatical determinations or procedures, to their preparation and to their use in such determinations or procedures. They are particularly useful in radioimmunoassay solid phase determinations.

2. Description of the Prior Art

Numerous solid phase immunochemical procedures are known. Typically, the biologically active reagent utilized is rendered insoluble prior to immune reaction by attachment to an insoluble carrier such as by physical adsorption, by covalent cross-linking or by covalent binding. In the case of radioimmunoassay, (RIA), an antibody is rendered insoluble prior to the reaction with labelled and unlabelled antigen.

Examples of various test tubes as insoluble carriers are disclosed in U.S. Pat. Nos. 3,721,528, 3,888,629, 3,768,979, 3,615,222, 3,865,552, 3,867,517 and 3,938,953. These patents show tubes, including two piece tubes, coated with various biologically active substances, such as antigens or antibodies. Insoluble particles as carriers are shown in U.S. Pat. Nos. 3,551,555, 3,639,558 and 3,553,310. The U.S. Pat. No. 3,551,555 discloses polymeric particles coated with an inert protein to which a biologically active substance is adsorbed. The U.S. Pat. No. 3,553,310 discloses polymeric particles coated with an inert protein to which a biologically active substance is coupled using an aldehyde. The U.S. Pat. No. 3,639,558 discloses polymeric particles to which an inert protein is coupled and having the biologically active substance coupled to the protein. An example of a slide and a microporous membrane are shown in U.S. Pat. No. 3,666,421 and German Pat. No. DT-2539-657. Various polymers and coupling agents are disclosed in U.S. Pat. Nos. 3,555,143, 3,857,931, 3,914,400, 3,826,619, 3,793,445, 3,949,064, 3,646,346, 3,853,987, 3,708,572 and 3,714,345.

Solid phase RIA procedures utilizing a biologically active reagent attached to an insoluble carrier were developed to simplify the separation of free antigen from antibody bound antigen. However, some of these currently available have one or more of the following disadvantages including excessive handling steps, poor reproducibility and/or sensitivity.

Consequently, a solid phase immunochemical procedure that provides fast and rapid separation and is accurate, sensitive and reproducible would be an advancement in the art.

SUMMARY OF THE INVENTION

In one aspect of this invention, there is provided an elongated hollow container suitable for use in an immunochemical or enzymatical procedure comprising (a) a lower reactive part composed of a polymeric material, said part being closed at one end and having on at least a portion of its inner surface a coating of an inert protein to which a biologically active substance is attached, and (b) a separable, inert upper part connected to and in communication with said lower part.

By using the above mentioned container in an immunochemical procedure a simple, easily conducted procedure is provided which is accurate, sensitive and reproducible. The separable parts lead to ease and uniformity of manufacturing, the provision of a substantially uniform coating of inert protein on one continuous surface for given immunochemical procedures; and consequently, to a more reliable and accurate determination or test. The coating of inert protein makes it possible to efficiently utilize the biologically active substance. The inert protein stabilizes the biologically active substance and increases its activity. It also provides a surface with constant characteristics. When the biologically active substance is attached by covalent binding, the amount that can be attached is increased. Covalent binding of the biologically active substance to the inert protein coating is easier to control than other forms of attachment. Moreover, bleeding or leaching of the biologically active substance into the reaction mixture is reduced by covalent binding thereby increasing accuracy and reproducibility of the immunochemical procedure.

Another aspect of this invention is directed to an elongated hollow container comprising (a) a lower reactive part composed of a polymeric material, said part being closed at one end and having at least a portion of both its inner surface and outer surface coated with an inert protein to which is attached a biologically active substance, and (b) a separable, inert upper part connected to and in communication with said lower part.

Another aspect is directed to a method of processing the foregoing containers, particularly on a large scale.

Another aspect is directed to the use of the foregoing containers in enzymatical and immunochemical procedures, particularly RIA procedures.

DETAILED DESCRIPTION OF THE INVENTION

As mentioned, the lower reactive part of the container is composed of a polymeric material or materials. Suitable polymeric materials that may be used in preparing the lower reactive part are well known to those skilled in the art. Such polymeric materials are typically substantially water insoluble, have a low affinity for the attached biologically active substance and are capable of being molded. Examples of such polymeric materials include organic polymers, such as hydrocarbon polymers, i.e., polystyrene, polyethylene, polypropylene, polybutylene, diazotized polystyrene, butyl rubber and other synthetic rubbers. Other suitable polymers are polyesters, polyamides, cellulose, cellulose derivatives, acrylates, methacrylates, and vinyl polymers such as polyvinyl chloride, and polyvinylidene. Additional satisfactory polymers include copolymers, such as substituted graft copolymers of polystyrene and polytetrafluoroethylene. Glass may also be used, typically that employed in test tubes or laboratory equipment. Because of their commercial availability and ease of use, especially useful polymers are copolymers of ethylene and acrylic acid. Typically, such copolymers contain from about 80 to 97 mole percent ethylene and from about 3 to 20 mole percent acrylic acid. Other preferable polymers include copolymers of acrylic acid and acrylamide; methyl methacrylate and acrylamide; methyl methacrylate and methacrylamide; and methyl methacrylate and acrylamide.

Preferably the lower reactive part is in the form of a conventional tube that is used in immunochemical procedures. The length of the lower reactive part may be any convenient size and in general is of sufficient length as necessary to provide the needed amount of biologically active substance for the immunochemical procedure or test involved. Generally, the length is from about 10 mm to 50 mm, preferably from about 15 mm to 25 mm, and optimally about 20 mm and the diameter is from about 5 mm to 20 mm, preferably 10 to 20 mm and optimally about 12 mm. A lower reactive part which is about 20 mm in length and having a diameter of about 12 mm will have a capacity of about 1.2 ml. Of course, the capacity is dependent on the length and diameter of the lower part. Use of the lower reactive part leads to ease of manufacturing. Additionally, less active ingredients and equipment are required. Further, the lower reactive part can be made from the most advantageous polymer for coating and attachment of a biologically active substance and the inert upper part can be advantageously formed from polypropylene or polyethylene both of which provide rigidity, are easy to work with and are relatively inexpensive.

To the reactive bottom part, in accordance with this invention, is attached an inert protein. The term inert protein means a protein which does not take part in the immunochemical reaction and does not adversely affect the biological substance. The proteins that can be used are well known to those skilled in the art. They include any proteinaceous material such as serum albumins or globulins obtained from various animal species or can be other uniform materials.

Particularly preferred are bovine gammaglobulin and gelatin which are readily available. Desirably, the proteinaceous material employed should be sufficiently homogenous so that an essentially continuous surface can be obtained by use thereof. Such a surface is readily obtainable with the above proteins.

A wide range of biologically active substances can be attached to the inert protein. Such substances include antigens and antibodies having immunological properties and enzymes having enzymatic properties.

Antigens may be defined as substances that stimulate the formation of antibody within an animal and that can react observably with that antibody. Antigens generally possess a high molecular weight of 10,000 or greater. A hapten is a low molecular weight substance which by itself cannot elicit an antibody response but when chemically coupled to a high molecular weight substance, e.g., a protein, can elicit an antibody response and the hapten can react with the resulting antibody. A detailed description of antigens is set forth in Principles of Immunology, Rose, Milgram and van Oss, eds., MacMillan Publishing Co., New York, N.Y. 1973.

In response to an injection of antigens, the body of an animal produces specific antibodies which react with and neutralize the antigens. Antibodies are classified as proteins with the solubility of globulins. Their molecular weight falls principally into two groups of approximately 160,000 designated as normal globulins and 1,000,000 designated as macroglobulins. The low molecular weight type predominates in most animal species. Heavy antibody is produced in the horse, cow and pig immunized with pneumococci, and in rabbits immunized with sheep red blood cells. The molecular weights of antibodies do not differ significantly from the molecular weights of globulins in normal sera of the various species. Of particular importance are the globulins which consist of a continuous series of proteins of a different physical and chemical properties and overlapping biological activities. They display wide variations in electrophoretic mobility, are salted out over a considerable range of electrolyte concentrations, yield many fractions by the alcohol precipitation method, and have sedimentation constants from 7 S to 20 S (Svedberg units).

Typical antibodies which may be attached to the inert protein include those against the haptens digoxin, triiodothyronine (T3), thyroxine (T4), TSH, angiotensin, and insulin; the various biologically active steroids; the bile acids; other polypeptide hormones; enzymes and isoenzymes; and pharmacologically active substances such as drugs of abuse as well as those used for therapy and others.

Enzymes which may be attached to the inert protein include diastase, glucose oxidase, urease, maltase, amylase, peroxidase, and other enzymes and coenzymes.

In accordance with the process of this invention, the lower reactive parts of the containers are prepared by a process which comprises (a) coating by adsorption the surface of a lower reactive part with an inert protein under adsorbing conditions, (b) attaching a biologically active substance to the inert protein coating of the lower reactive part of (a) under attaching conditions, (c) treating the lower reactive part of (b) having the biologically active substance attached to the inert protein coating with a stabilizing agent to stabilize such biologically active substance against denaturization, and (d) drying the reactive part (c) under drying conditions that will not substantially denature the biologically active substance. The containers of this invention are then prepared by attaching the inert upper part to the lower reactive part.

The amount of inert protein utilized giving optimum results is dependent on the nature of the inert protein, the reactive part and the biological substances. This amount is readily determinable by those skilled in the art. Typically, only a thin film e.g., at least one layer of molecules thick, of protein is attached to the surface. Generally, this is a sufficient amount to effect a uniform coating to which the biologically active substance may be attached.

The inert protein is readily attached to the surface to form a coating by spraying, soaking or, preferably by immersing the reactive bottom part in an aqueous solution of inert protein, preferably an aqueous buffer solution under coating conditions. In this manner the protein is adsorbed to the surface of the reactive bottom part. It is advantageous to utilize aqueous phosphate buffer solutions. Such buffers are described in U.S.P. XIX and are generally prepared utilizing dipotassium hydrogen phosphate and potassium dihydrogen phosphate. The appropriate amounts are disolved in water to produce the desired pH and the pH adjusted if necessary with KOH or HCl. If desired, a bacteriostatic agent to inhibit the growth of microorganisms may be added to the buffer solution such as sodium azide or thimerosal.

The inert protein is coated under adsorbing conditions which will not lead to denaturization of the protein. Specific pH and temperature conditions depend on the particular inert protein. Adsorbing conditions include conventional pH's, e.g. about 3 to 10 and conventional temperatures, e.g., about 20° C. to 30° C. While lower and higher application temperatures may be employed, for example as low as 4° C. and as high as 50° C., there is no significant advantage. In fact, at temperatures in excess of 50° C., the protein is generally denatured. At temperatures lower than 4° C. the protein is difficult to apply. For example, bovine gamma globulin is coated generally at a pH of 5 to 7 optimally 6.4 at room temperature.

To facilitate attachment of the inert protein, the surface of the lower reactive part prior to attachment may be treated with various materials to enhance adsorption of the inert protein. Such materials include solvents, surfactants, acids or bases.

Surfactants, advantageously, sodium dodecyl sulfate, are utilized as a detergent to clean the surface and make it wettable. If the polymers contain carboxyl groups on the surface, often it is desirable to treat them with a salt-forming base, e.g. KOH to convert them to the salt form, thus giving them a negative charge which provides for enhanced electrical attraction further enhancing adsorption. The base also helps to clean the surface. In another aspect, it is advantageous to make the charge distribution on the surface about equal to that of the inert protein to be applied. This is accomplished by washing the surface with an aqueous buffer solution having about the same pH as the coating solution containing the inert protein prior to coating.

The biologically active substance may be attached by any suitable means. Such suitable means known to the art include adsorption, covalent binding, ionic binding and entrapment. It is preferred to attach the biologically active substance by covalent binding because it is easier to control the coupling reaction and the product is more stable.

Methods for chemically i.e. covalently binding the biologically active substances to the inert protein are disclosed in U.S. Pat. Nos. 3,553,310 and 3,639,558, all of which are incorporated herein by reference. A preferred method of covalent binding of the biologically active substance to inert protein is by first treating the protein with an aldehyde coupling agent, followed by application of the biologically active substance under conditions to permit the aldehyde to covalently bind to both inert protein and the biologically active substance. Suitable aldehyde coupling agents are those which have either $\alpha,\beta$ unsaturation (ethylenic) or a plurality of aldehyde groups or both. Because of ease and convenience it is preferred to use an aldehyde selected from the group of an $\alpha, \beta$ unsaturated aldehyde, a dialdehyde or mixtures thereof to form aldehyde reaction products with the inert protein coating. The $\alpha, \beta$ unsaturated aldehydes, may be a compound having a formula of the type

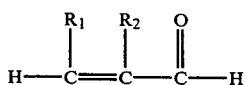

wherein anyone of $R_1$ or $R_2$ can be hydrogen or a methyl group. Representative of this type of aldehyde are acrolein, methaacrolein and 2-butenal. Dialdehydes can be employed such as glutaraldehyde, propanedial and butanedial.

When one of these aldehydes is contacted with the surface of the inert protein, the protein is stabilized and polymerized by cross-linking and aldehyde active moieties are fixed to the surfaces. These moieties are believed to be carbonyl groups and as such are highly reactive to the amine groups of biologically active substance since they form covalent bonds between the protein particles and the biologically active substances.

Alternative to aldehydes there may be used other coupler materials such as compounds having two or more of the following reactive groups: azo, sulfonic acid, fluoro groups activated by nitro groups, azide, imine and reactive chloro groups connected to a ring having proper resonance structure. These reactive groups are capable of reacting with the primary amino, sulfylhydryl, carboxylic, hydroxyl and phenolic groups in the substances constituting the inert protein as well as the biological substances to be coupled thereto.

A representative list of such coupling agents is bis-diazobenzadine, disulfonic acid, tetraazo-p-phenylenediamine difluorodinitrobenzene, difluorodinitrophenylsulfone, a carbodiimide, toluene diisocyanate, cyanuric chloride, dichlorotriazine, N-t-butyl-5-methyl is oxazolium perchlorate. Carbodiimides which can be employed are N, N-dicylcohexylcarbodiimide 1-ethyl-3(3-dimethylamino-propyl) carbodiimide hydrochloride and 1-cyclohexyl-3(2-morpholinyl(4)-ethyl carbodiimide) metho-p-toluene sulfonate.

Alternatively the above mentioned biologically active substances can be attached by adsorption according to the procedure described in U.S. Pat. No. 3,551,555.

The amount of coupling agent utilized in the preferred process of this invention will depend upon the particular inert protein and the biologically active substance to be coupled. This amount can be readily determined by those skilled in the art but typically it will be an amount to cross-link the inert protein and provide sufficient sites for coupling to the inert protein sufficient biologically active substance for carrying out the desired immunochemical or enzymatical procedure. In the case of aldehydes generally this is an amount from 0.1 to about 10% (w/v), preferably about 1 to about 2% (w/v).

Typically the coupling agent is applied in an aqueous buffer solution most advantageously a phosphate buffer which may contain other ingredients such as antioxidants, and bacteriostatic agents. The coupling agent may be applied at any convenient pH, for example, from about 3 to about 10. The coupling agent may be applied conveniently at room temperature. Lower temperatures may be utilized, for example as low as 4° C. but temperatures lower than 4° C. do not provide any significant advantage. Higher temperatures, for example, up to 50° C. Likewise may be employed but such temperatures do not provide any significant advantage. In the case of aldehydes the pH is generally from about 6 to 8 and the temperature is generally from about 20° to 30° C.

To facilitate attachment of the coupling agent to the inert protein, the protein is advantageously washed with the same buffer without the coupling agent prior to treatment with the buffer containing the coupling agent. Since the coupling agent is most stable at the pH of the buffer solution, this washing provides an environment most suitable to the stability of the coupling agent.

The amount of biologically active substance utilized in the practice of this invention will depend on the nature of the inert protein and the particular biologically active substance. Such amounts can readily be determined by those skilled in the art. Typically, it will be an amount sufficient to carry out the determination or procedure in which it will be utilized. For example in the case of a certain digoxin antiserum the dilution (i.e., parts of antiserum containing antibody/parts of treatment solution) is from about 1/300,000 to about 1/360,000 preferably 1/325,000 to 1/335,000.

The biologically active substance is advantageously applied in an aqueous solution preferably an aqueous phosphate buffer solution. It is applied under attaching conditions which will not denature the protein which includes applying at room temperature but higher or lower temperatures may be employed and at any convenient pH in the range of from 3 to about 10. Temperatures as low as 4° C. or lower and as high as 50° C. can conveniently be utilized. However, no significant advantage is gained by utilizing temperatures above 50° C. A pH of generally 6 to 7 is employed in the case of antibodies to digoxin, triiodothyronine and thyroxine.

In another aspect, the present invention involves the use of a protective agent to further protect the biologically active substance against denaturization during application and is generally employed in an amount effective to provide such protection by diminishing denaturization factors. For instance, the protective agent is present in much larger amounts than the biologically active substance and it protects by becoming denatured first as the biologically substance is applied. It is particularly advantageous to use these agents in large scale manufacturing operations. These agents include bovine serum albumin or other protective proteins that will not adversely affect the biological substance or the adsorbed protein coating. In the case of bovine serum albumin it is generally used in an amount of from about 0.05% (w/v) to about 1% (w/v), preferably 0.1 to about 0.2% (w/v).

To facilitate attachment of the biologically active substance, prior to applying it to the reactive part, the reactive part is advantageously washed with the same buffer the biologically active substance will be in.

After the biologically active substance is applied it is preferable to immediately remove any excess unreacted biologically active substance. In the case of antibodies it is advantageously accomplished by treating with an amino acid buffer solution having a pH of generally about 1 to 3. A glycine sodium chloride buffer is preferred. After this treatment the reactive parts are preferably treated with a buffer solution having a pH generally in the range of 6 to 8 to raise the pH to nearly neutral.

Next the lower reactive part is treated with a stabilizing agent to stabilize the activity of the coupled biological active substance against denaturization. Such a stabilizing agent is a polyvinyl alcohol which has a viscosity of 4-6 (4% (w/v) solution) centipoise at 20° C. It is generally applied in an effective stabilizing amount for example 2% (w/v). It is usually applied in an aqueous buffer solution preferably a phosphate buffer at room temperature. Generally the pH of this buffer solution depends on the pH at which the biologically active substance is most stable. After treatment with the stabilizing agent, the lower reactive part is drained and dried under drying conditions that do not lead to denaturation of the biologically active substance. It is advantageous to use vacuum drying. Any commercial dryer may be employed, using drying temperatures generally of 10° to 45° C. preferably 25° to 35° C.

Between each of the above mentioned steps it is preferable to use several water washes to be sure there is no carry over contamination. Generally, the treating solutions are stirred at a rate during their application which will not adversely affect the inert protein, inert protein coating, biologically active substance or inert protein coating to which is attached the biologically active substance or cause excessive bubble formation but sufficient to insure complete mixing and to accomplish the appropriate treatment. For example in the case of the inert protein treating solution, the rate of stirring can be easily determined by running a number of batches at various rates and then determining the optimum rates. The same procedure may be used to determine the rate for the treating solutions containing the aldehyde, biologically active substance and for the various buffer solutions.

Generally, about 6 parts of treating solution are used for each lower reactive part. More or less may be used for example about 2 to 12 parts per lower reactive part.

The separable inert upper part in accordance with this invention may be any one of the above mentioned polymers including glass. By inert it is meant that the part will not influence the biological substances taking part in the immunochemical test detrimentally. Typically used polymers for ease of convenience and because of their low cost include polypropylene and polyethylene. Additionally they provide rigidity. As will be appreciated the purpose of the inert upper part is to provide suitable capacity to carry out the immunochemical or enzymatical procedure. Usually this part is made up of a portion or portions which are open at both ends and attached to the lower reactive part. It may be attached by any suitable means, to provide a leak free (e.g. water tight) container. For example, the bottom part may be designed to snugly fit over the top part. The upper part may also be attached by heat sealing or other suitable means known to those persons skilled in the art. The size of the inert upper part can vary according to the immunochemical or enzymatical procedures employed and this will be readily known to those skilled in the art. Generally, the length is from about 50 mm to about 100 mm, preferably from about 55 mm to about 80 mm and optimally 65 mm. The diameter is generally about the same as the lower reactive part.

BRIEF DESCRIPTION OF DRAWINGS

Reference will now be made to the drawing to illustrate a preferred embodiment of this invention. FIG. 1 shows a device of this invention in tube form. FIG. 2 shows the inert upper part. FIG. 3 shows the lower reactive part. Lower reactive Part 1 has a coating of inert protein to which the biological substance is attached on its inner surface 3 and its outer surface 4. The inert separable upper Part 2 is attached to lower reactive Part 1.

In a preferred embodiment of this invention the lower reactive parts of the containers of this invention have on both the inner and outer surface of the reactive part a coating of inert protein to which the biologically active substance is attached by covalent binding.

Another aspect of this invention is the use of these separation systems in immunochemical procedures or determinations, to determine antigen or hapten concentrations, particularly with advantage in RIA determinations or tests. Such RIA procedures and the techniques for carrying them out are well known to those skilled in the art. They will be described in more detail in the following examples.

EXAMPLE 1

Preparation of Containers of This Invention 1,300 lower reactive parts having the shape shown in FIG. 3, having a capacity of 1.1 ml. and composed of a polymer of polyethylene and acrylic acid (92 mole percent polyethylene and 8 mole percent acrylic acid) were prepared as follows.

(1) The 1,300 untreated lower parts were immersed in a stainless steel or polyethylene container containing 7800 ml. of 0.5% aqueous sodium dodecyl sulfate (SDS) solution and stirred for 30 minutes at room temperature. (2) The SDS solution was removed, replaced with 7800 ml. of water and the parts were then washed for 5 minutes. This washing procedure was repeated twice. (3) The water was removed, replaced with 7800 ml. of an aqueous 0.2 N potassium hydroxide solution, and the parts were stirred for 30 minutes in this solution. (4) The potassium hydroxide solution was then removed, replaced with water and the parts were washed for 5 minutes. This washing procedure was repeated until the pH of the final wash solution was 7.0. (5) The water was removed, replaced with an aqueous solution of 0.1 M phosphate (pH 6.4) containing 0.1% bovine gamma globulin and 0.1% sodium azide and the parts were then stirred for 30 minutes in this solution. (6) The gamma globulin solution was removed, replaced with water and the lower reactive parts washed for 5 minutes. This washing procedure was repeated three times. (7) The water was replaced by 7800 ml. of a phosphate buffer solution (0.1 M; pH 7.4) containing 2% glutaraldehyde and the lower parts were stirred for 30 minutes at room temperature in this solution. (8) The glutaraldehyde solution was removed, replaced by 7800 ml. of water and the parts were washed for 10 minutes. This washing procedure was repeated twice. (9) The water was replaced by an aqueous phosphate buffer solution (0.01 M; pH 7.0) containing digoxin antibodies (from goat) 1:160,000 dilution, normal goat serum 1:32,000 dilution, 0.1% bovine serum albumin and 0.01% sodium azide, the lower parts were then stirred for one-half hour at room temperature in this solution. (10) The treating solution was replaced by 7800 ml. of water and the lower reactive parts were washed 10 minutes. This washing procedure was repeated twice. (11) The water was replaced with 7800 ml. of an aqueous glycine sodium chloride buffer solution (0.1 M; pH 2.3) and the parts were washed for 30 minutes at room temperature. (12) The glycine buffer solution was removed and replaced by 7800 ml. of 0.1 M pH 7.4 phosphate buffer solution and the parts were washed for 10 minutes. This washing procedure was repeated once. (13) The phosphate buffer was removed, replaced with 7800 ml. of an aqueous phosphate buffered saline solution (0.01 M; pH 7.4 0.9% NaCl) and the lower parts were stirred in this solution for 30 minutes at room temperature. (14) The phosphate buffered saline was removed and replaced by 7800 ml. of pH 7.4 0.01 M phosphate buffer containing 2% polyvinylalcohol and 0.01% sodium azide and the pieces stirred for 30 minutes. (15) The lower reactive parts were vacuum dried for about two hours. (16) To the reactive lower parts were attached inert upper parts by snapping the two together to thereby provide a conventional test tube suitable for use in solid phase RIA procedures. The inert upper part was composed of polypropylene and was about 3.25 inches long.

EXAMPLE 2

RIA Procedure

In a conventional test tube rack place 12 digoxin antibody coated tubes prepared according to this invention. To each tube pipette 1 ml. of digoxin reaction mixture containing I-125 digoxin in phosphate buffer solution (0.01 M phosphate, pH 7.4 0.9% sodium chloride). To each tube pipette 100 μl of standard serum in the appropriate dilution of digoxin, i.e., 0 ng per ml. into tubes 1 and 2; 0.4 ng per ml. into tubes 3 and 4; 1 ng per ml. into tubes 5 and 6; 2 ng per ml. into tubes 7 and 8; 3 ng per ml. into tubes 9 and 10 and 5 ng per ml into tubes 11 and 12. Gently agitate the rack for 5 to 10 seconds and then incubate in a water bath for about one hour at about 37° C. Remove the rack and then decant the contents of all the tubes carefully. Dispense two ml. of distilled water into each of the tubes and decant. Count the tubes in a gamma counter for one minute. Calculations are made as follows:

1. Calculate the net counts per minute for all standards by subtracting the average instrument background count.
2. Express the corrected count rate for each set of standards as a percentage of the average (0 ng per ml.) standard count rate (% B*/Bo**)

$$\% \ B/BO = \frac{\text{corrected counts per minute of standard}}{\text{corrected counts per minute of (0 ng per ml.)}} \times 100$$

*—B = percent bound in all other tubes
**—Bo = percent bound in the 0 ng per ml. standard 3. Using semi-log graph paper, plot the % B/Bo for each standard concentration against the concentration of digoxin as ng per ml.

Actual Procedure

The following results were obtained following the above procedure:

| Sample (ng/ml) | Postcount (net) (cpm) | B/B (%) |
|---|---|---|
| 0 | 6202 | 100% |
|  | 6006 (av.) |  |
|  | 5810 |  |
| 0 |  |  |
| 0.4 | 4886 | 81.4 |
| 0.4 | 4920 | 81.9 |
| 1.0 | 4032 | 67.1 |
| 1.0 | 3960 | 65.9 |
| 2.0 | 2232 | 37.2 |
| 2.0 | 2470 | 41.1 |
| 3.0 | 1712 | 28.5 |
| 3.0 | 1725 | 28.7 |
| 5.0 | 1247 | 20.8 |
| 5.0 | 1023 | 17.0 |

A graph of the above results indicates the sensitivity and reproducibility of the test.

EXAMPLE 3

The procedure given in Example 1 was followed to coat lower reactive parts with antibody to triiodothyronine (T$_3$), except that the antibody coating solution dilution in step (9) was 1:10,000 and the normal goat serum was omitted. Batches of several hundred lower reactive parts were prepared, adjusting the volume of treating solution on the basis of 6.0 ml. per part. These parts were then used to determine triiodothyronine uptake in serum samples.

EXAMPLE 4

The following solutions are employed to process the containers of this invention described below.

Reagents to Make One Liter of Solution

1. Phosphate Buffer, 0.1 M, pH 6.4 (I)
   a. Add, with stirring, 9.96 g Potassium Dihydrogen Phosphate to water.
   b. To the solution from 1a, add 4.66 g Dipotassium Hydrogen Phosphate.
   c. Dilute to 900 ml with water and add 1.0 g Sodium Azide. Measure the pH with a pH meter. If the pH is outside of the range 6.3–6.5, adjust with KOH or HCl solutions as required.
   d. Dilute to one liter.
2. Phosphate Buffer 0.1 M, pH 7.4 (II)
   a. Add, with stirring, 2.66 g Potassium Dihydrogen Phosphate to water.
   b. Add, with stirring, 14.00 g Dipotassium Hydrogen Phosphate to solution 2a.
   c. Dilute solution 2b to 900 ml and measure the pH with a meter. If not between pH 7.3–7.5, adjust with KOH or HCl solutions as necessary.
   d. Dilute solution 2c to one liter.
3. Phosphate Buffer, 0.01 M, pH 7.0, 0.01% Sodium Azide (III)
   a. Add to water, with stirring, 0.533 g Potassium Dihydrogen Phosphate.
   b. To solution 3a, add, with stirring, 1.056 g Dipotassium Hydrogen Phosphate.
   c. Dilute solution 3b to 900 ml with water and add 100 ml Sodium Azide. Measure the pH with a meter. Adjust, if necessary, between pH 7.0–7.1 with KOH or HCl Solution.
   d. Dilute solution 3c to one liter.
4. Glycine Buffer, 0.1 M, pH 2.3 (I)
   a. Add, with stirring, 7.5 g Glycine and 5.85 g Sodium Chloride to 600 ml $H_2O$.
   b. To solution 4a, add 5.3 ml concentrated HCl and dilute to 900 ml. If the pH is outside of the range 2.3–2.4, adjust with KOH or HCl solutions as necessary. Dilute with water to 1.0 ml.

Preparation of Containers Using Above Solutions 100 lower reactive parts having the shape shown in FIG. 3, having a capacity of 1.1 ml. and composed of a polymer of polyethylene and acrylic acid (92 mole percent polyethylene and 8 mole percent acrylic acid) were prepared as follows.

(1) The 100 untreated lower parts were immersed in a stainless steel or polyethylene container containing 600 ml. of 0.5% aqueous sodium dodecyl sulfate (SDS) solution and stirred for 60 minutes at room temperature. (2) The SDS solution was removed, replaced with 600 ml. of water and the parts were then washed for 5 minutes. This washing procedure was repeated twice. (3) The water was removed, replaced with 600 ml. of an aqueous 0.2 N potassium hydroxide solution, and the parts were stirred for 30 minutes in this solution. (4) The potassium hydroxide solution was then removed, replaced with water and the parts were washed for 5 minutes. This washing procedure was repeated until the pH of the final wash solution was 7–8. The water was removed and replaced with phosphate buffer (I) and the parts were washed for 5 minutes. (5) The water was removed, replaced with phosphate buffer (I) containing 0.05% bovine gamma globulin and the parts were then stirred for 30 minutes in this solution. (6) The gamma globulin solution was removed, replaced with water and the lower reactive parts washed for 5 minutes. This washing procedure was repeated twice. The water was removed and replaced with phosphate buffer (II) and the parts were washed for 5 minutes. (7) The water was replaced by 600 ml. of a phosphate buffer II containing 2% glutaraldehyde and the lower parts were stirred for 60 minutes at room temperature in this solution. (8) The glutaraldehyde solution was removed, replaced by 600 ml. of water and the parts were washed for 5 minutes. This washing procedure was repeated twice. The water was removed and replaced with phosphate buffer (III) and the parts were washed for 5 minutes. (9) The water was replaced by phosphate buffer (III) containing digoxin antibodies (from goat) 1:325,000–1:335,000 dilution, 0.1% bovine serum albumin, the lower parts were then stirred for two hours at room temperature in this solution. (10) The treating solution was replaced by 600 ml. of water and the lower reactive parts were washed 5 minutes. (11) The water was replaced with 600 ml. of glycine buffer (I) and the parts were stirred for 30 minutes at room temperature. (12) The glycine buffer was removed and replaced by 600 ml. of phosphate buffer (II) and the parts were washed for 5 minutes. This washing procedure was repeated twice. (13) The phosphate buffered was removed and replaced by 600 ml. of phosphate buffer (II) containing 2% polyvinyl alcohol and the pieces stirred for 30 minutes. (14) The lower reactive parts were vacuum dried for about two hours. (15) To the reactive lower parts were attached inert upper parts by snapping the two together to thereby provide a conventional test tube suitable for use in solid phase RIA procedures. The inert upper part was composed of polypropylene and was about 3.25 (60 mm) inches long.

EXAMPLE 5

The procedure given in Example IV was followed to coat lower reactive parts with antibody to triiodothyronine ($T_3$), except that the antibody coating solution dilution in step (9) was 1:300,000 and the antibody was from goats. Batches of several hundred lower reactive parts were prepared adjusting the volume of treating solution on the basis of 6.0 ml per part.

EXAMPLE 6

The procedure given in Example IV was followed to coat lower reactive parts with antibody to thyroxine ($T_4$) except that the antibody coating solution dilution in step (9) was 1:2000 and the antibody was from rabbits. Batches were prepared adjusting the volume of treating solution on the basis of 6.0 ml per part.

EXAMPLE 7

T4-RIA

In a conventional test tube rack place 14 thyroxine antibody coated tubes prepared according to this invention. To each tube pipette 1 ml. of thyroxine reaction mixture containing veronal buffer (0.076 M, pH 8.6), 0.01% sodium azide, Mg ANS, 900 µg/ml. and 200 pg/ml I-125 thyroxine, 0.1 µC/ml. To each tube except two pipette 25 µl of standard serum in the appropriate dilution of thyroxine, i.e., 0 ng per ml. into tubes 1 and 2; 2.0 ng per ml. into tubes 3 and 4; 5 ng per ml. into tubes 5 and 6; 10 ng per ml. into tubes 7 and 8; 20 ng per ml. into tubes 9 and 10 and 40 ng per ml. into tubes 11 and 12. To tubes 13 and 14 pipette 25 μl of unknown sera. Gently agitate the rack for 5 to 10 seconds and then incubate in a water bath for about one hour at about 37° C. Remove the rack and then decant the contents of all the tubes carefully. Dispense two ml. of distilled water into each of the tubes and decant. Count the tubes in a gamma counter for one minute. Calculations are made as follows:

1. Calculate the net counts per minute for all standards by subtracting the average instrument background count.
2. Express the corrected count rate for each set of standards as a percentage of the average (0 ng per ml.) standard count rate (% B*/BO**)

$$\% \ B/BO = \frac{\text{corrected counts per minute of standard}}{\text{corrected counts per minute of (0 ng per ml.)}} \times 100$$

*—B = percent bound in all other tubes
**—Bo = percent bound in the 0 ng per ml. standard 3. Using semi-log graph paper, plot the % B/Bo for each standard concentration against the concentration of T4 as ng per ml.

Actual Procedure

The following results were obtained following the above procedure:

| Sample (ng/ml) | Average Postcount (net) (cmp) | B/B (%) |
| --- | --- | --- |
| 0 | 32591 | 100% |
| 2 | 25525 | 78.3 |
| 5 | 20909 | 64.2 |
| 10 | 14774 | 45.8 |
| 20 | 9916 | 30.4 |
| 40 | 6802 | 20.9 |
| Unknown | 17603 | 54.0 |

A graph of the above results indicates the sensitivity and reproducibility of the test.

EXAMPLE 8

T3 Uptake Test

In a conventional test tube rack place 6 T3 antibody coated tubes prepared according to this invention. To each tube pipette 1 ml. of T3 reaction mixture containing 0.05 M tris-(hydroxymethyl)amino methane, pH 7.3, 0.05%, sodium azide, 100 pg/ml I-125 triiodothyronine. To each of 3 tubes pipette 25 μl of standard serum, to the other 3 pipette 25 microliters of unknown sera. Gently agitate the rack for 5 to 10 seconds and then incubate in a water bath for about one hour at about 20°–26° C. Remove the rack and then decant the contents of all the tubes carefully. Dispense two ml. of distilled water into each of the tubes and decant. Count the tubes in a gamma counter for one minute. Calculations are made as follows:

1. Calculate the net counts per minute for all standards by subtracting the average instrument background count.
2. Calculate the Thyro Binding Capacity (TBC) Index for each serum sample by the following formula $$\frac{\text{NET } CPM \text{ STANDARD}}{\text{NET } CPM \text{ UNKNOWN}} \times \text{Normalizing Factor*} = TBC \text{ Index}$$

*Determined from standard serum.

As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. An elongated, hollow container suitable for use in an immunochemical or enzymatical procedure comprising
   (a) a lower reactive part composed of a polymeric material, said part being closed at one end and having on at least a portion of its inner surface a coating of an inert protein to which a biologically active substance is attached; and
   (b) a separable inert upper part connected to and in communication with said lower part.

2. In an immunochemical or enzymatical method for determining the concentration of a member selected from the group consisting of an antigen and hapten in a measured amount of an aqueous sample wherein said aqueous solution is contacted with (1) an insoluble carrier to which has been attached a biologically active substance capable of reacting with said member and (2) a measured amount of tracer labelled member to form after substantial equilibration a 2-phase system containing a solid phase having a portion of the labelled member and unlabelled member bound to said biologically active substance and a liquid phase containing the balance of the unbound labelled member and unlabelled member, the two phases separated and the concentrated determined, the improvement comprising using as the insoluble carrier the container of claim 1.

3. In a radioimmunoassay method for determining the concentration of a member selected from the group consisting of an antigen and hapten in a measured amount of an aqueous sample wherein said aqueous sample is contacted with (1) an insoluble carrier to which has been attached a biologically active substance capable of reacting with said member and (2) a measured amount of radioactively labelled member to form after substantial equilibration a 2-phase system containing a solid phase having a portion of the labelled member and unlabelled member bound to said biologically active substance and a liquid phase containing the balance of the unbound labelled member and unlabelled member, the 2-phases separated and the radioactivity of at least one of the phases being measured, the value of radioactivity being a function of the concentration of said member in the aqueous sample, the improvement comprising using as the insoluble carrier the container of claim 1.

4. A method according to claim 3 wherein said biologically active substance is an antibody.

5. A method according to claim 4 wherein said reactive part has said coating on a portion of its inner surface and a portion of its outer surface.

6. A method according to claim 5 wherein said antibody is covalently bound to said inert protein through a coupling agent which contains $\alpha,\beta$ unsaturation, carbonyl groups, azo groups, sulfonic acid groups, fluoro groups activated by nitro groups, azide groups, imine groups or reactive chloro groups connected to ring structures.

7. A method according to claim 6 wherein the container is in the form of a tube.

8. A method according to claim 7 wherein said inert protein is gelatin of bovine gamma globulin.

9. A method according to claim 8 wherein said reactive part is composed of a copolymer of polyethylene and acrylic acid.

10. A method according to claim 9 wherein said biologically active substance is covalently bound with an aldehyde coupler.

11. A method according to claim 10 wherein said antibody is an antibody to triiodothyronine, thyroxine or digoxin.

12. A method according to claim 11 wherein said inert protein is bovine gamma globulin said coupler is glutaraldehyde and said lower part is composed of a copolymer of polyethylene and acrylic acid and said upper part is polypropylene.

13. A process for preparing the lower reactive part of claim 1 which comprises
    (a) coating by adsorption the surface of a lower reactive part, composed of a polymeric material, said part being closed at one end with an inert protein under adsorbing conditions
    (b) attaching a biologically active substance to the inert protein coating on the lower reactive part of (a) under attaching conditions
    (c) treating the lower reactive part of (b) having the biologically active substance attached to the inert protein coating with a stabilizing agent to stabilize such biologically active substance against denaturization and
    (d) drying the reactive part under drying conditions that will not substantially denature the biologically active substance.

14. A process according to claim 13 wherein the biologically active substance is attached to the inert protein coating by covalent binding through a coupling agent which contains $\alpha,\beta$ unsaturation, carbonyl groups, azo groups, sulfonic acid groups, fluoro groups activated by nitro groups, azide groups, imine groups or reactive chloro groups connected to ring structures.

15. A process according to claim 14 wherein said biologically active substance is an antibody.

16. A process according to claim 15, wherein the inert protein is contained in a phosphate buffer solution, the antibody is contained in a phosphate buffer solution, the coupling agent to covalently bind the antibody is contained in a phosphate buffer solution, and the stabilizing agent is contained in a phosphate buffer solution.

17. A process according to claim 16 wherein said phosphate buffer solution containing the antibody additionally contains an inert protein to retard denaturization of the antibody.

18. A process according to claim 17 wherein said antibody is covalently bound with an aldehyde coupler.

19. A process according to claim 18 wherein said reactive part is composed of a copolymer of polyethylene and acrylic acid.

20. A process according to claim 19 wherein said inert protein adsorbed on the surface is bovine gamma globulin and said inert protein to retard denaturization of the antibody is bovine serum albumin.

21. A process according to claim 20 wherein said antibody is an antibody to triiodothyronine, thyroxine or digoxin.

22. A process according to claim 21 wherein said stabilizer is polyvinyl alcohol.

23. A process according to claim 22 wherein said lower reactive part is dried utilizing vacuum drying.

24. A process for preparing a lower reactive part, composed of a copolymer of polyethylene and acrylic acid, said part being closed at one end and having on at least a portion of its inner surface a coating of the inert protein bovine gamma globulin to which digoxin antibody is attached which comprises:
    (a) cleaning with 0.5% by weight, based on the total volume of the solution, of an aqueous solution of sodium dodecyl sulfate the surface of a lower reactive part, composed of a copolymer of polyethylene, 92% by weight and acrylic acid, 8% by weight, said part being closed at one end and thereafter washing one or more times with water,
    (b) treating the lower reactive part of (a) with a sufficient amount of an aqueous solution of potassium hydroxide to convert the carboxyl groups on the surface to the salt form, washing one or more times with water and then with a phosphate buffer solution having a pH of about 6.4,
    (c) coating by adsorption the surface of the lower reactive part of (b) by immersing in a phosphate buffer solution containing the inert protein bovine gamma globulin under adsorbing conditions and thereafter washing with water one or more times and then washing with a phosphate buffer solution having a pH of about 7.4,
    (d) coupling sufficient glutaraldehyde to enable attachment of antibody to digoxin to the bovine gamma globulin coating on the reactive part of (c) by immersing said reactive part in a phosphate buffer solution having a pH of about 7.4, containing about 2% by weight based on the total volume of the solution of glutaraldehyde, thereafter washing with water one or more times and then washing with a phosphate buffer solution having a pH of 7.0,
    (e) coupling antibody to digoxin to the glutaraldehyde on the reactive part of (d) by immersing said reactive part in a phosphate buffer solution having a pH of 7.0, containing antibody to digoxin in a dilution of 1/325,000 to 1/335,000 and a protective agent, bovine serum albumin, to retard denaturization of said antibody under attaching conditions, washing with water one or more times and then washing with a glycine buffer solution having a pH of about 2.4 to remove any antibody not coupled to the glutaraldehyde,
    (f) washing one or more times with a phosphate buffer solution having a pH of about 7.4 and thereafter treating with a phosphate buffer solution having a pH of about 7.4 containing 2% by weight, based on the total volume of the solution, polyvinyl alcohol as a stabilizing agent, and
    (g) vacuum drying under conditions which will not substantially denature the antibody.

25. A method for preparing an elongated hollow container suitable for use in an immunochemical or enzymatical procedure comprising attaching a separable inert upper part to the lower reactive part of claim 33 so that said inert upper part is in communication with said lower part.

26. An elongated, hollow container suitable for use in an immunochemical or enzymatical procedure comprising
    (a) a lower reactive part composed of a polymeric material containing carboxylate salt groups, said part being closed at one end and having attached on at least a portion of its inner surface a coating of an inert protein to which a biologically active substance, stabilized against denaturization, is attached by means of a chemical coupling agent through which said biologically active substance is covalently bound to said inert protein; and (b) a separable inert upper part connected to and in communication with said lower part.

27. A container according to claim 26 wherein said biologically active substance is an antibody.

28. A container according to claim 27 wherein said reactive part has said coating on a portion of its inner surface and a portion of its outer surface.

29. A container according to claim 28, wherein said antibody substance is covalently bound to said inert protein through a coupling agent which contains $\alpha,\beta$ unsaturation, carbonyl groups, azo groups, sulfonic acid groups, fluoro groups activated by nitro groups, azide groups, imine groups or reactive chloro groups connected to ring structures.

30. A container according to claim 29 in the form of a tube.

31. A container according to claim 29 wherein said inert protein is gelatin or bovine gammaglobulin.

32. A container according to claim 29 wherein said reactive part is composed of a copolymer of ethylene and acrylic acid.

33. A container according to claim 29 wherein said biologically active substance is covalently bound with an aldehyde coupler.

34. A container according to claim 29 wherein said antibody is an antibody to triiodothyronine, thyroxine or digoxin.

35. A container according to claim 29 wherein said inert protein is bovine gammaglobulin, said coupler is glutaraldehyde said lower part is composed of a copolymer of polyethylene and acrylic acid and said upper part is polypropylene.

36. A process for preparing the lower reactive part of claim 26 which comprises (a) coating by adsorption the surface of a lower reactive part composed of a polymeric material containing carboxylate salt groups, said part being closed at one end, with an inert protein under adsorbing conditions (b) attaching a biologically active substance to the inert protein coating on the lower reactive part of (a) under attaching conditions by means of a chemical coupling agent through which said biologically active substance is covalently bound to said inert protein (c) treating the lower reactive part of (b) having the biologically active substance attached to the inert protein coating with a stabilizing agent to stabilize such biologically active substance against denaturization and (d) drying the reactive part under drying conditions that will not substantially denature the biologically active substance.

* * * * *